(12) United States Patent
Mohankumar et al.

(10) Patent No.: US 10,488,324 B2
(45) Date of Patent: Nov. 26, 2019

(54) METHODS FOR DETECTING FAILURE OF AN ADHESIVE LAYER

(71) Applicant: Toyota Motor Engineering & Manufacturing North America, Inc., Erlanger, KY (US)

(72) Inventors: Prasanth Mohankumar, Canton, MI (US); Paul D. Cowan, Pinckney, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 197 days.

(21) Appl. No.: 15/601,284

(22) Filed: May 22, 2017

(65) Prior Publication Data

US 2018/0335397 A1 Nov. 22, 2018

(51) Int. Cl.
*G01N 19/04* (2006.01)
*G01N 25/72* (2006.01)
*B32B 37/12* (2006.01)

(52) U.S. Cl.
CPC .............. *G01N 19/04* (2013.01); *B32B 37/12* (2013.01); *G01N 25/72* (2013.01)

(58) Field of Classification Search
CPC ...................................................... G01N 19/04
USPC ........................................................ 73/150 A
See application file for complete search history.

(56) References Cited

U.S. PATENT DOCUMENTS

| 6,505,391 | B1 | 1/2003 | Berna | |
|---|---|---|---|---|
| 6,800,157 | B2* | 10/2004 | Tarbutton | C08G 59/182 156/73.5 |
| 9,333,736 | B2* | 5/2016 | Kumakura | B32B 43/006 |
| 2014/0150970 | A1* | 6/2014 | Desai | C08G 59/184 156/320 |
| 2014/0326074 | A1* | 11/2014 | Van Voast | G01N 19/04 73/827 |
| 2015/0059987 | A1* | 3/2015 | Kumakura | B32B 43/006 156/714 |

(Continued)

FOREIGN PATENT DOCUMENTS

| CN | 202994575 U | 6/2013 |
|---|---|---|
| JP | 2016221784 A | 12/2016 |

OTHER PUBLICATIONS

Adams et al. "Durability of Adhesively Bonded Joints for Aircraft Structures" Researchgate article. Uploaded May 15, 2015. (Year: 2015).*

(Continued)

*Primary Examiner* — Nathaniel J Kolb
(74) *Attorney, Agent, or Firm* — Dinsmore & Shohl LLP (57) ABSTRACT

A method for detecting failure of an adhesive layer applied to first and second surfaces includes inserting a first wedge between the first and second surfaces adhered to one another by the adhesive layer to separate the first and second surfaces by a first predetermined distance, inspecting the adhesive layer for failure when the first and second surfaces are separated by the first predetermined distance, inserting a second wedge between the first and second surfaces to separate the first and second surfaces by a second predetermined distance, and inspecting the adhesive layer for failure when the first and second surfaces are separated by the second predetermined distance.

18 Claims, 3 Drawing Sheets

(56) References Cited

U.S. PATENT DOCUMENTS

2016/0033388 A1* 2/2016 Raeckers ............... G01N 19/04
73/827

OTHER PUBLICATIONS

Blackman et al. "The impact wedge-peel performance of structural adhesives" J. Materials Science, vol. 35, 2000, 1867-1884 (Year: 2000).*
Sener et al. "On the precision of the wedge-opened double cantilever beam method for measuring the debonding toughness of adhesively bonded plates." International Journal of Adhesion and Adhesives 22 (2002) 129-137 (Year: 2002).*

* cited by examiner

METHODS FOR DETECTING FAILURE OF AN ADHESIVE LAYER

TECHNICAL FIELD

The present specification generally relates to methods for detecting adhesive layer failures and, more specifically, methods for detecting adhesive layer failures in automotive manufacturing processes.

BACKGROUND

During automotive manufacturing processes, various components may be coupled to one another using adhesives, such as when various panels are adhered to one another for form the roof of a vehicle. However, during subsequent steps of the manufacturing process, the panels and adhesive are exposed to increased temperatures, which cause expansion of the panels, and may lead to adhesive failure when the expansion occurs after the adhesive has fully cured.

Conventional methods used to evaluate and select adhesives have included testing the adhesives on static panels, which does not account for the stresses imparted on the adhesive layer during the manufacturing process. Accordingly, a need exists for alternative methods for predicting and detecting adhesion failure during automotive manufacturing processes.

SUMMARY

In one embodiment, a method for detecting failure of an adhesive layer applied to first and second surfaces may include inserting a first wedge between the first and second surfaces adhered to one another by the adhesive layer to separate the first and second surfaces by a first predetermined distance, inspecting the adhesive layer for failure when the first and second surfaces are separated by the first predetermined distance, inserting a second wedge between the first and second surfaces to separate the first and second surfaces by a second predetermined distance, and inspecting the adhesive layer for failure when the first and second surfaces are separated by the second predetermined distance.

In another embodiment, a method for selecting an adhesive for use in an automotive manufacturing process may include applying a layer of a first adhesive between first and second panels effective to adhere the first panel to the second panel, heating the first adhesive layer, the first panel, and the second panel to a predetermined temperature, inserting a first wedge between the first and second panels to separate the first and second panels by a first predetermined distance, and inspecting the first adhesive layer for failure when the first and second panels are separated by the first predetermined distance. The method further includes inserting a second wedge between the first and second panels to separate the first and second panels by a second predetermined distance, inspecting the first adhesive layer for failure when the first and second panels are separated by the second predetermined distance, and selecting an adhesive from a group of adhesives including the first adhesive based on the inspecting.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
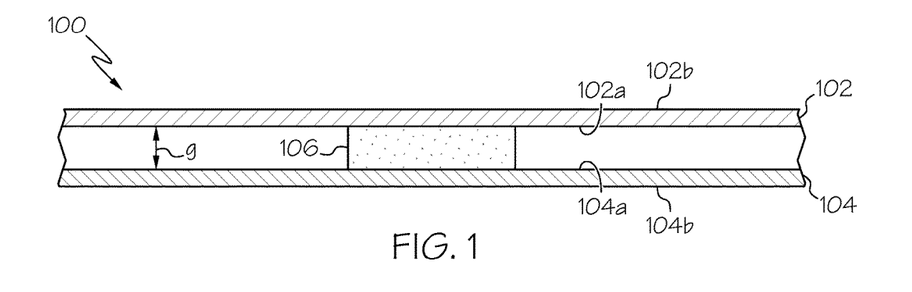
FIG. 1 depicts a cross-sectional view of first and second panels adhered together by an adhesive layer according to one or more embodiments shown and described herein.

FIG. 1 generally depicts one embodiment of an assembly 100 including a first panel 102 and a second panel 104 adhered to one another by an adhesive layer 106. As will be described herein, the adhesive used in the adhesive layer 106 can be evaluated for failure by separating the first panel 102 from the second panel 104 by a predetermined distance and inspecting the adhesive layer 106. Various embodiments of the evaluation method and a jig for use in separating the first panel from the second panel will be described in more detail herein.

Referring now to FIG. 1, the assembly 100 includes a first panel 102 and a second panel 104 separated from one another by a gap g and adhered to one another by an adhesive layer 106. More particularly, the first panel 102 includes a first surface 102a and a second surface 102b opposite the first surface 102a. The first surface 102a and the second surface 102b are separated by a thickness of the first panel 102. In various embodiments, the thickness may be constant along an entire length and width of the first panel 102.

Similar to first panel 102, the second panel 104 includes a first surface 104a and a second surface 104b opposite the first surface 104a. The first and second surfaces 104a, 104b are separated by a thickness of the second panel 104. In various embodiments, the thickness may be constant along an entire length and width of the second panel 104.

Each of the first and second panels may be made from one of a variety of materials suitable for use in the desired application. For example, in embodiments in which the first and second panels are adhered to one another to form an automotive roof, each of the panels may be made from a material, such as, by way of example and not limitation, steel, aluminum, or fiberglass. In some embodiments, the first panel is made from a first material while the second panel is made from a second material that is different from the first. Accordingly, in various embodiments, the first panel may have a linear thermal expansion coefficient that differs from a linear thermal expansion coefficient of the second panel.

The adhesive layer 106 may be formed from any suitable type of adhesive, although in various embodiments, the adhesive layer is formed from a mastic adhesive. The mastic may be naturally-derived or synthetic. In various embodiments, the mastic may be applied between the first and second panels to avoid chafing between the panels, and to keep the panels in place relative to one another.

Because of the differences between the linear thermal expansion coefficients of the first and second panels, when the assembly including the first and second panels and the adhesive is heated, the first panel 102 may bow or flex in a direction away from the second panel 104, increasing a distance between the first panel 102 and the second panel 104 along at least a portion of the assembly. In embodiments in which the distance between the panels occurs at or near an area where the adhesive layer 106 is positioned, the movement of the first panel 102 may cause the adhesive layer 106 to expand. However, when the temperature reaches a cure temperature of the mastic, the mastic cures and no longer expands. Accordingly, further movement of the first panel 102 away from the second panel 104 may result in failure of the adhesive layer 106.

In order to determine whether a particular adhesive is likely to fail during the manufacturing process, in various embodiments, an assembly including a first panel 102, a second panel 104, and an adhesive layer 106 may be exposed to heat and separated in order to simulate the reaction of the assembly to the conditions present in the manufacturing process. In general, the testing method includes inserting a first wedge between the panels to separate the panels by a predetermined distance, inspecting the adhesive layer for failure when the panels are separated by the predetermined distance, inserting a second wedge between the panels to separate the panels by a second predetermined distance, and inspecting the adhesive layer for failure when the panels are separated by the predetermined distance. The process will now be described in additional detail.

In various embodiments, an assembly is prepared for use in the method. For example, the first panel and/or second panel may be optionally subjected to one or more treatments that are used in the automotive manufacturing process. As but one non-limiting example, at least one of the first and second panels may be prepared using an oiling dip and drip method in which the panel is dipped into one or more stamping oils and then drained to remove excess oil from the surface of the panel. Other surface treatments may be applied, depending on the particular embodiment.

Once the panels have been subjected to the optional surface treatment, a layer of an adhesive is applied between the first and second panels effective to adhere the first panel to the second panel. For example the adhesive can be placed on the second panel 104 before the first panel 102 is put into place. The amount of adhesive may vary depending on the particular embodiment. In some embodiments, the adhesive may be applied as a drop having a diameter of from about 10 mm to about 15 mm. Alternatively, the adhesive may be applied as a series of drops, as a line, or in another pattern.

In some embodiments, optional spacers may be positioned between the panels in order to simulate a weld gap that may be found between panels. The spacers may be from about 1 mm to about 5 mm, and in some particular embodiments, about 3 mm, in height. In various embodiments, the spacers may be placed on the second panel 104, and the first panel 102 may then be positioned over the spacers and adhesive layer 106. The spacers may be placed at any suitable location between the panels to maintain the distance d between the first panel 102 and the second panel 104. In some particular embodiments, each spacer is from about 10 mm to about 20 mm from the adhesive layer 106. Accordingly, in various embodiments, panels may be pushed toward one another such that the first surface 102a of the first panel 102 is separated from the first surface 104a of the second panel 104 by a distance d equal to the height of the spacer.

In various embodiments, an oven is heated to a predetermined temperature in preparation for the testing. The predetermined temperature may be, for example, between about 80° C. and about 210° C., from about 100° C. to about 200° C., or from about 140° C. to about 190° C. Other temperatures may be selected based on the particular embodiment. For example, the predetermined temperature may be selected based at least in part on environmental conditions to which the panels and adhesive are exposed during manufacturing or use.

In some embodiments, a weight may be used to maintain the position of the first panel 102 with respect to the second panel 104 during the testing. In such embodiments, the weight may be of any suitable weight to maintain the distance d between the first panel 102 and the second panel 104. For example, in some embodiments, the weight may be from about 0.5 kilogram (kg) to about 5 kg, from about 1 kg to about 2.5 kg, or from about 1.5 kg to about 2 kg. In one embodiment, the weight is in the form of an iron bar, although other weights of various shapes and sizes may be employed.

In embodiments utilizing a weight to maintain the position of the first panel 102 with respect to the second panel 104, the weight may be placed in the oven to be preheated prior to placement on the assembly. Without being bound by theory, it is believed that if the weight is not preheated, it may act as a heat sink, enabling the first panel 102 to remain cool while in the oven during the testing, and adversely impacting the results of the test. However, when the weight is preheated to the first predetermined temperature prior to placing the assembly in the oven, the weight allows energy transfer between the weight and the first panel 102, and allows the first panel 102 to heat up upon exposure to the conditions within the oven, thereby effectively simulating real world conditions during manufacturing.

In some embodiments, a weight is not employed. For example, in embodiments in which one or more non-expanding materials are used for the first panel 102, the second panel 104, and/or the adhesive layer 106, a weight may not be needed. Alternatively, in some embodiments, clamps, clips, welds, or the like, may be employed along the edges of the assembly to prevent over-expansion of the assembly during heating.

After the oven and optional weight are preheated to the predetermined temperature, the assembly may be placed in the oven and heated for a predetermined time. For example, the assembly may be placed in the oven, the weight may be positioned on top of the first panel 102 and in contact with the second surface 102b of the first panel 102. The predetermined time may be any amount of time from about 3 minutes to about 30 minutes. For example, in various embodiments, the predetermined time may be from about 5 minutes to about 20 minutes. In some particular embodiments, the predetermined time may be 5 minutes, 10 minutes, 15 minutes, 20 minutes, or the like. The amount of time may be selected, for example, on the particular conditions to be simulated, the predetermined temperature, a cure time of the adhesive, or a combination thereof.

After the assembly is heated in the oven for the predetermined time, in various embodiments, the heated assembly is removed from the oven. However, it is contemplated that in some embodiments, the test may be conducted while the assembly remains in the oven, provided that the assembly can be accessed and inspected. In some embodiments, the weight and/or the spacers may be removed from the assembly, although in other embodiments, the test may be conducted with the weight and/or spacers in place.

To test the adhesive layer, the first panel 102 and the second panel 104 are separated from one another by one or more predetermined distances and the adhesive is inspected while the panels are separated. In embodiments in which the test is conducted outside of the oven, the panels may be separated and the adhesive may be inspected within a short period of time after removal from the oven. For example, in various embodiments, the test is conducted within one minute from the removal of the assembly from the oven, within 45 seconds, within 30 seconds, or within 15 seconds of the removal of the assembly from the oven. Without being bound by theory, it is believed that when the testing is performed substantially immediately after the baking, the panels and adhesive layer may be at the temperature of the oven and will best simulate the manufacturing conditions of interest. Separation of the panels will now be described in greater detail.

Figure 2:
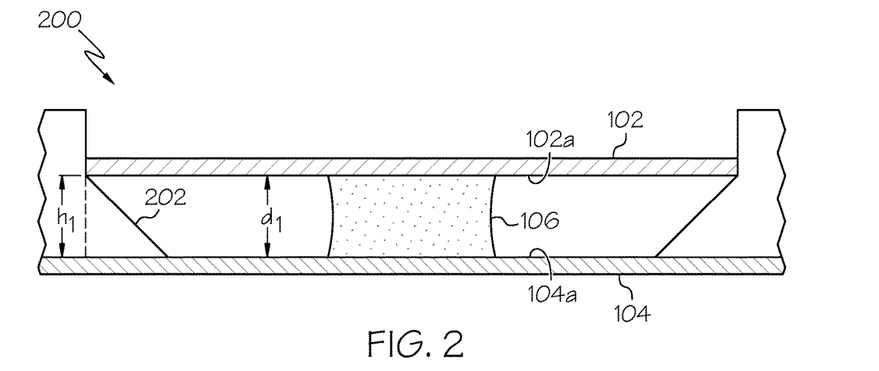
FIG. 2 depicts a cross-sectional view of first and second panels adhered together by an adhesive layer being separated by a first predetermined distance according to one or more embodiments shown and described herein.

Turning now to FIG. 2, an assembly 200 is which the first panel 102 and the second panel 104 are separated from one another by a first predetermined distance, $d_1$. More specifically, a first surface 102a of the first panel 102 is separated from a first surface 104a of the second panel 104 by the predetermined distance $d_1$ by a first wedge 202. The first wedge 202 has a height $h_1$, which corresponds to the first predetermined distance $d_1$. In some embodiments, two wedges 202 are inserted to separate the first panel 102 from the second panel 104, one at a first end of the assembly 200 and one at a second end of the assembly 200 opposing the first end. It is contemplated that a greater or fewer number of wedges may be employed, depending on the particular embodiment. However, in various embodiments, at least two wedges are employed to ensure that the panels 102 and 104 are separated by the first predetermined distance along the length of the assembly.

In various embodiments, the first predetermined distance may be from about 1 mm to about 10 mm, from about 4 mm to about 7 mm, or from about 5.5 mm to about 6.5 mm. Other distances may be selected for the first predetermined distance, depending on the particular embodiment. For example, when the first panel 102 is made from an aluminum metal, which tends to move a greater amount when exposed to heat than, for example, steel, a larger predetermined distance may be selected. The first predetermined distance may also depend, for example, on the type of adhesive employed in the particular embodiment. For example, for adhesives that have higher cure temperatures, a larger predetermined distance may be selected.

After the panels are separated by the first predetermined distance, the adhesive layer 106 is inspected for failure. The inspection may be conducted, for example, manually by an operator who visually inspects the adhesive layer 106, or the inspection may be automated. For example, a camera may be used to capture one or more images of the adhesive layer 106 when the first panel 102 is separated from the second panel 104 by the first predetermined distance $d_1$, and image processing software may be used to identify failure in the adhesive layer 106.

In some embodiments, image processing software may receive an image of the adhesive layer 106 captured while the panels are separated by the first predetermined distance, such as by a camera, and compare the image to reference images of adhesive layers exhibiting failure to determine if the adhesive layer 106 is exhibiting failure. For example, if one or more features within the captured image matches one or more features in the reference image(s), failure of the adhesive may be identified. Alternatively, the image processing software may compare the captured image to reference images of adhesive layers not exhibiting failure to determine if the adhesive layer 106 is exhibiting failure. For example, if one or more features within the captured image do not match one or more features in the reference image(s), failure of the adhesive may be identified. In still other embodiments, the image processing software may recognize certain features indicative of failure of the adhesive layer, such as gaps between the adhesive layer and at least one surface to which the adhesive layer is to be adhered, an amount of necking, or separation within the adhesive layer, as will be described in greater detail below.

Figure 3:
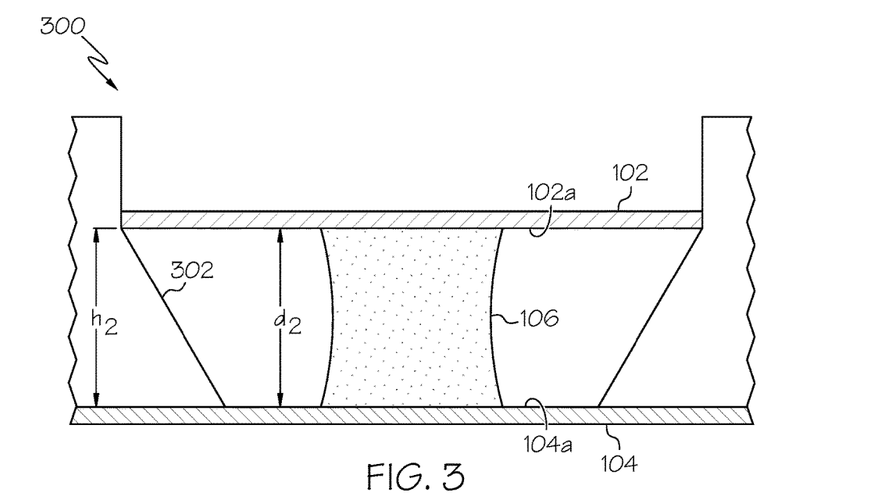
FIG. 3 depicts a cross-sectional view of first and second panels adhered together by an adhesive layer being separated by a second predetermined distance according to one or more embodiments shown and described herein.

When failure is observed, the test is concluded. However, in embodiments in which failure in the adhesive layer 106 is not observed, the wedge(s) are removed, and a second wedge 302 is inserted between the first panel 102 and the second panel 104, as depicted in FIG. 3. Specifically, in FIG. 3, an assembly 300 is depicted in which the first surface 102a of the first panel 102 is separated from the first surface 104a of the second panel 104 by a second predetermined distance $d_2$ by the second wedge 302. The second wedge 302 has a height $h_2$, which corresponds to the second predetermined distance $d_2$. As above, in some embodiments, two wedges 302 are inserted to separate the first panel 102 from the second panel 104, one at a first end of the assembly 300 and one at a second end of the assembly 300 opposing the first end, as is shown in FIG. 3. However, it is contemplated that a greater or fewer number of wedges may be employed, depending on the particular embodiment.

In various embodiments, the second predetermined distance may be from about 3 mm to about 20 mm, from about 7 mm to about 10 mm, or from about 8.5 mm to about 9.5 mm. Other distances may be selected for the second predetermined distance, depending on the particular embodiment. For example, when the first panel 102 is made from an aluminum metal, which tends to move a greater amount when exposed to heat than, for example, steel, a larger predetermined distance may be selected. The second predetermined distance may also depend, for example, on the type of adhesive employed in the particular embodiment. For example, for adhesives that have higher cure temperatures, a larger predetermined distance may be selected. However, in various embodiments, the first predetermined distance is less than the second predetermined distance.

After the panels are separated by the second predetermined distance, the adhesive layer 106 is inspected for failure. As above, the inspection may be conducted, for example, manually by an operator who visually inspects the adhesive layer 106, or the inspection may be automated.

It is contemplated that in some embodiments, additional iterations of inserting wedges and inspecting the adhesive layer for failure may be conducted. For example, a third wedge or set of wedges may be used to separate the first panel from the second panel by a third predetermined distance that is greater than the second predetermined distance.

The results of each inspection of the adhesive layer may be recorded, for example, using a computing device. In various embodiments, the computing device may include one or more processors capable of executing machine readable instructions stored in a memory component. The memory component may be configured as a volatile and/or nonvolatile non-transitory computer readable medium and, as such, may include random access memory (including SRAM, DRAM, and/or other types of random access memory), flash memory, registers, compact discs (CD), digital versatile discs (DVD), magnetic disks, and/or other types of storage components. Additionally, the memory component may be configured to store, among other things, operation logic and data, such as data captured by an automatic inspection system (e.g., a camera) or externally acquired data, in the form of user input of results of the inspection.

In embodiments, the computing device may also include a communication pathway to provide signal interconnectivity between various components of the computing device. In some embodiments, the communication pathway may further provide signal interconnectivity between the other system components within the computing device. Accordingly, the communication pathway may be formed from any medium that is capable of transmitting a signal such as, for example, conductive wires, conductive traces, optical waveguides, or the like. The computing device may also include one or more network interface modules, to connect the computing device to a remote computing device or a remote computer network, such as a control unit for the oven, an automatic inspection system, or the like. The network interface module may include any wired or wireless networking hardware, such as a modem, LAN port, wireless fidelity (Wi-Fi) card, WiMax card, mobile communications hardware, and/or other hardware for communicating with other networks and/or devices. Thus, in some embodiments, the communication pathway may facilitate the transmission of wireless signals, such as WiFi, Bluetooth, and the like.

In various embodiments, multiple adhesives may be tested and the results recorded using the computing device (either automatically or by way of a user input of the result data), thereby enabling comparison of the performance of a group of adhesives. For example, in some embodiments, an adhesive may be selected from a group of adhesives for use in an automotive manufacturing process based on the results of the test. For example, assemblies may be prepared as described above using first and second adhesives. Then, each assembly may be separated and inspected as described according to FIGS. 2 and 3 above. As an example, if failure of the second adhesive is observed in response to separating the panels by the second predetermined distance, but failure of the first adhesive is not observed in response to separating the panels by the second predetermined distance, the first adhesive may be selected.

In some embodiments, the results of the inspection may be one of multiple factors used to select an adhesive from a group of adhesives. For example, cost, chemical composition, and other business factors may further be considered. However, in various embodiments, the selection is based at least in part on the results of the inspection.

Figure 4:
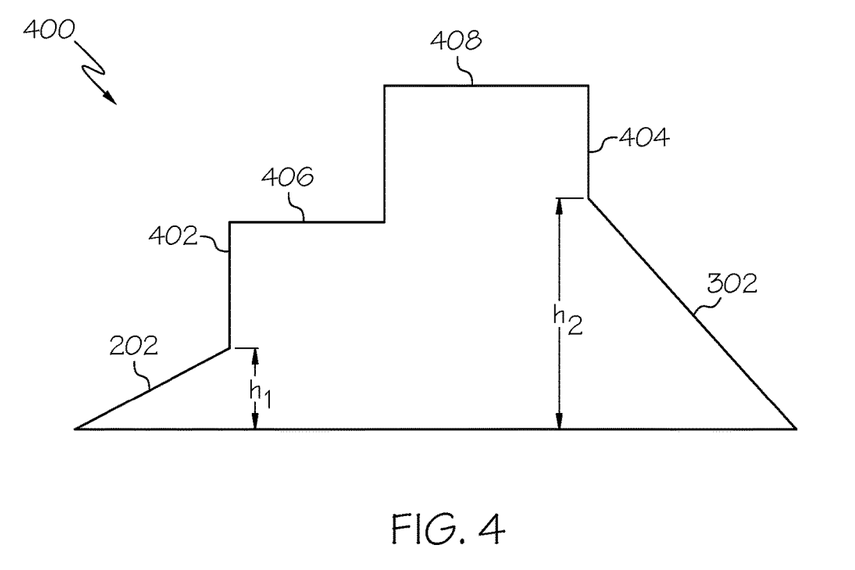
FIG. 4 depicts a side view of a jig for use in separating panels according to one or more embodiments shown and described herein.

Having explained the test method in detail, consider now a jig for use in the testing method, such as the jig 400 depicted in FIG. 4. The jig 400 includes the first wedge 202 having a first height $h_1$ and the second wedge 302 having a second height $h_2$. In the embodiment depicted in FIG. 4, the first wedge 202 and the second wedge 302 are on opposing sides of the jig 400, although it is contemplated that in some embodiments, the first wedge 202 may be on a side that is adjacent to a side having the second wedge 302. For example, in some embodiments, the jig 400 may include four wedges or more, each wedge positioned on a side of the jig 400.

The jig 400 may be formed from a metal, such as aluminum or steel, or may be formed from a plastic or other material, such as wood. In various embodiments, the jig 400 is formed from a material that is able to withstand temperatures of greater than about 150° C., 175° C., 190° C., or even 200° C. or higher, such that the jig 400 does not melt or deform when it is placed in contact with the assembly.

Adjacent to the first wedge 202 is a first stopping face 402 in the form of a substantially vertical surface extending upward from the top of the first wedge 202. In various embodiments, the first stopping face 402 may prevent the jig 400, and particularly the first wedge 202, from being inserted too far between the first panel 102 and the second panel 104, or from not being inserted far enough to separate the first panel 102 from the second panel 104 by the first predetermined distance $d_1$. Accordingly, in various embodiments, a user may push the first wedge 202 between the first and second panels until the first stopping face 402 contacts the edge of the first panel 102, thereby preventing the first wedge 202 from being inserted too far between the panels. The first stopping face 402 may have any suitable height. For example, in some embodiments, the first stopping face 402 may extend from the top of the first wedge 202 a distance of from about 10 mm to about 30 mm, or from about 12 mm to about 18 mm, or even from about 14 mm to about 16 mm. The height of the first stopping face 402 may vary depending on the particular embodiment. For example, when the jig 400 is to be used with thicker panels, the height of the first stopping face 402 may be greater than a height of the first stopping face 402 in embodiments in which the jig 400 is to be used with thin panels.

Similarly, adjacent to the second wedge 302 is a second stopping face 404. Like the first stopping face 402, the second stopping face may be a substantially vertical surface extending upward from the top of the second wedge 302. The second stopping face 404 may prevent the second wedge 302 from being inserted too far between the first panel 102 and the second panel 104 while ensuring that the first panel 102 is separated from the second panel 104 by the second predetermined distance $d_2$. The second stopping face 404 may have any suitable height. For example, in some embodiments, the second stopping face 404 may extend from the top of the second wedge 302 a distance of from about 10 mm to about 30 mm, or from about 12 mm to about 18 mm, or even from about 14 mm to about 16 mm. In some embodiments, the height of the second stopping face 404 may be larger than the height of the first stopping face 402. However, it is contemplated that the height of the second stopping face 404 may be smaller than the height of the first stopping face 402, or the first and second stopping faces may have the same height.

Although various embodiments include the first and second stopping faces, it is contemplated that in other embodiments, the jig may include only one stopping face or no stopping faces. Furthermore, in embodiments in which the jig includes more than two wedges, each wedge may have a corresponding stopping face to prevent over-insertion of the wedge.

In the embodiment depicted in FIG. 4, the jig 400 further includes a first top face 406 and a second top face 408. The first top face 406 extends substantially horizontally from the top of the first stopping face 402 toward the opposing side of the jig 400 while the second top face 408 extends substantially horizontally from the second stopping face 404. Although FIG. 4 is depicted as including two top faces, it is contemplated that in some embodiments, such as when the first and second stopping faces extend to the same distance from a bottom of the jig, a single top face may be employed. Additionally, in embodiments in which more than two wedges are included, additional corresponding top faces may further be included in the jig 400.

In various embodiments, the first top face 406 and the second top face 408 may enable the user to readily ascertain which side of the jig 400 corresponds to the first wedge 202 and which side of the jig 400 corresponds to the second wedge 302. For example, the first top face 406 may be lower in height as compared to the second top face 408, indicating that the first wedge 202 is on the left side of the jig 400, as shown in FIG. 4. In practice, the ease of identification may assist the user with readily orienting and inserting the appropriate wedge when the assembly is removed from the oven.

Figure 5:
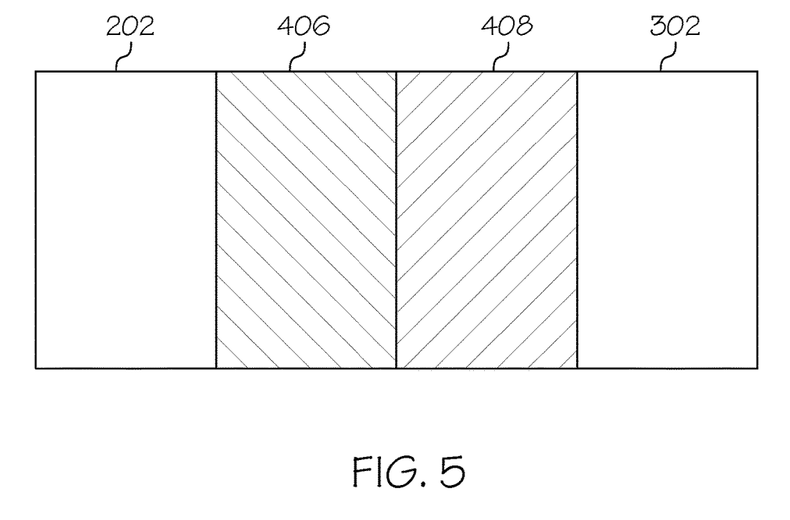
FIG. 5 depicts a top view of the jig of FIG. 4 according to one or more embodiments shown and described herein.

Alternatively, as depicted in the top view of the jig 400 shown in FIG. 5, the first top face 406 may have a first visual indicator while the second top face 408 may have a second visual indicator that is different from the first visual indicator. The visual indicator may be, for example, a color, pattern, image, or other marking useful to designate the wedge on a corresponding side of the jig. In some embodiments, the visual indicator may be in the form of a numerical marking, such as a "1" or "2", indicating which wedge is to be inserted first and second, or "6" or "10", indicating a height of the corresponding wedge.

As provided above, in various embodiments, after the assembly including the first panel 102, the second panel 104, and the adhesive layer 106 is baked in the oven and the panels are separated by a predetermined distance, the assembly, and in particular, the adhesive layer 106, is inspected for signs of failure. As used herein, "failure" may refer to adhesive failure of the adhesive layer, or it may refer to cohesive failure of the adhesive layer.

Figure 6A:
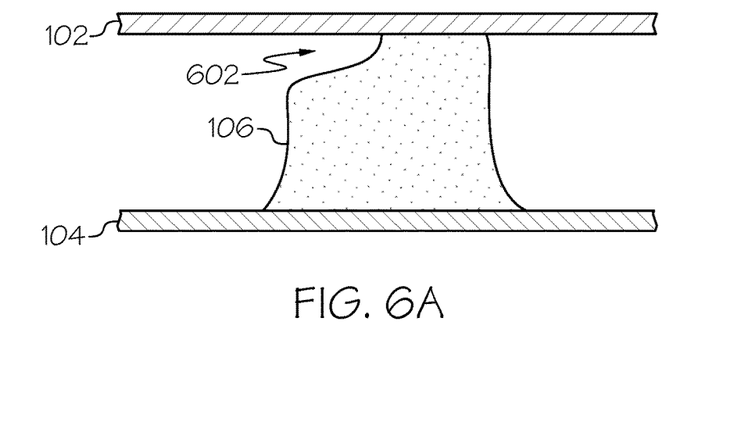
FIG. 6A depicts an example of adhesive failure according to one or more embodiments shown and described herein.

FIG. 6A depicts an embodiment in which adhesive failure 602 is observed. As used herein, "adhesive failure," sometimes referred to as interfacial fracture or adhesive fracture, is when debonding occurs between the adhesive in the adhesive layer 106 and at least one surface, such as a surface of the first panel 102 or the second panel 104. Specifically, in FIG. 6A, the adhesive layer 106 has pulled away from at least a portion of the first panel 102. Accordingly, in various embodiments, failure of the adhesive during inspection may be identified when the adhesive layer 106 at least partially separates from one or both surfaces to which the adhesive layer 106 was bonded or when the adhesive layer 106 fully separates from one or both surfaces to which the adhesive layer 106 was bonded.

Figure 6B:
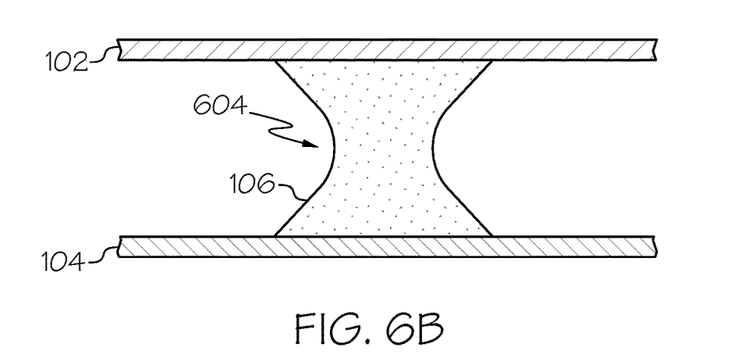
FIG. 6B depicts an example of extreme necking according to one or more embodiments shown and described herein.

However, not all failure occurs between the adhesive layer and the surfaces of the panels. In some embodiments, such as the embodiment shown in FIG. 6B, failure may be in the form of extreme necking 604. As used herein, the term "necking" refers to the thinning of a center of an adhesive during a tensile test. In various embodiments, necking, and in particular, extreme necking, of the adhesive failure may be indicative of impending cohesive failure. "Extreme necking" refers to necking such that a minimum width of the adhesive layer has a width of about 50% or less of a maximum width of the adhesive layer, a width of about 40% or less of a maximum width of the adhesive layer, a width of about 30% or less of a maximum width of the adhesive layer, a width of about 25% or less of maximum width of the adhesive layer, or even a width of about 10% or less of maximum width of the adhesive layer. The amount of extreme necking that corresponds to failure may vary depending on the particular embodiments, although in some embodiments, the minimum width of the adhesive layer is from about 1% to about 50% of the maximum width of the adhesive layer, from about 1% to about 45%, from about 1% to about 30%, or from about 1% to about 25% of the maximum width of the adhesive layer.

Figure 6C:
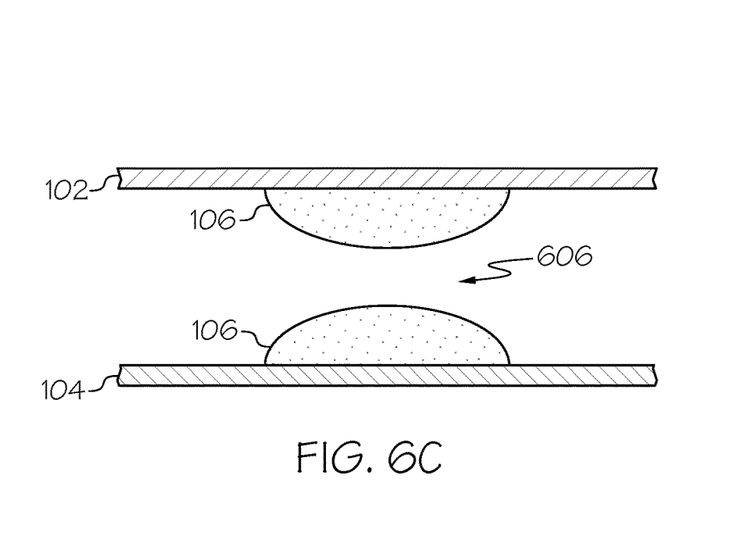
FIG. 6C depicts an example of cohesive failure according to one or more embodiments shown and described herein.

FIG. 6C depicts an embodiment in which cohesive failure 606 is observed. As used herein, "cohesive failure," sometimes referred to as cohesive fracture, is when debonding occurs within the adhesive layer 106. In particular, following cohesive failure, the adhesive layer 106 remains bonded to both the first panel 102 and the second panel 104. Cohesive failure may occur near the center of the adhesive layer 106, such as is shown in FIG. 6C, or near an interface. For example, the adhesive layer portion bonded to the first panel 102 following cohesive failure near the interface between the adhesive layer 106 and the first panel 102 be smaller than the adhesive layer portion bonded to the second panel 104.

Accordingly, various embodiments described herein enable detection of the failure of an adhesive that may occur during manufacturing or during use. Detection of the failure of the adhesive may enable manufacturing processes to be modified, or may enable adhesives to be evaluated for selection for use in manufacturing processes based at least in part on expected failures. For example, in some embodiments, the detection of the failure of an adhesive may be used at least partially to select one adhesive for use from a group of potential adhesives. By simulating conditions to which the adhesive will be subjected to, failure of the adhesive can be anticipated and adjustments may be made to avoid issues in production.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for detecting failure of a first adhesive layer comprising a first adhesive applied to first and second surfaces, comprising:

inserting a first wedge between the first and second surfaces adhered to one another by the first adhesive layer to separate the first and second surfaces by a first predetermined distance;

inspecting the first adhesive layer for failure when the first and second surfaces are separated by the first predetermined distance;

inserting a second wedge between the first and second surfaces to separate the first and second surfaces by a second predetermined distance; and inspecting the first adhesive layer for failure when the first and second surfaces are separated by the second predetermined distance, wherein failure comprises at least partial separation from at least one of the first and second surfaces or cohesive failure within the first adhesive layer.

2. The method of claim 1, further comprising:

applying the first adhesive layer to the first surface;

positioning the second surface in contact with the first adhesive layer, wherein the first surface opposes the second surface; and heating the first adhesive layer, the first surface, and the second surface to a predetermined temperature prior to inserting the first wedge.

3. The method of claim 2, wherein predetermined temperature is between 80° C. and about 210° C.

4. The method of claim 2, wherein the method further comprises:

preheating a weight; and positioning the weight on the first adhesive layer, the first surface, and the second surface during the heating.

5. The method of claim 1, wherein the first predetermined distance is less than the second predetermined distance.

6. The method of claim 1, the method further comprising:

inserting the first wedge between a third and a fourth surface adhered to one another by a second adhesive layer comprising a second adhesive to separate the third and fourth surfaces by the first predetermined distance;

inspecting the second adhesive layer for failure when the third and fourth surfaces are separated by the first predetermined distance;

inserting the second wedge between the third and fourth surfaces to separate the third and fourth surfaces by the second predetermined distance;

inspecting the second adhesive layer for failure when the third and fourth surfaces are separated by the second predetermined distance; and selecting one of the first adhesive and the second adhesive for use in a manufacturing process based on the inspecting.

7. The method of claim 1, wherein the first adhesive layer comprises a mastic adhesive.

8. The method of claim 1, wherein at least one of the first and second surfaces is a metal surface.

9. The method of claim 1, wherein the first predetermined distance is from about 1 mm to about 10 mm.

10. The method of claim 9, wherein the first predetermined distance is from about 4 mm to about 7 mm.

11. The method of claim 1, wherein the second predetermined distance is from about 3 mm to about 20 mm.

12. The method of claim 11, wherein the second predetermined distance is from about 7 mm to about 10 mm.

13. A method of selecting an adhesive for use in an automotive manufacturing process, the method comprising:

applying a layer of a first adhesive between first and second panels effective to adhere the first panel to the second panel;

heating the first adhesive layer, the first panel, and the second panel to a predetermined temperature;

inserting a first wedge between the first and second panels to separate the first and second panels by a first predetermined distance;

inspecting the first adhesive layer for failure when the first and second panels are separated by the first predetermined distance;

inserting a second wedge between the first and second panels to separate the first and second panels by a second predetermined distance;

inspecting the first adhesive layer for failure when the first and second panels are separated by the second predetermined distance; and selecting an adhesive from a group of adhesives including the first adhesive based on the inspecting, wherein failure consists of at least partial adhesive failure or at least partial cohesive failure.

14. The method of claim 13, wherein the predetermined temperature is from about 80° C. to about 210° C.

15. The method of claim 13, wherein the group of adhesives further comprises a second adhesive, the method further comprising:

applying a layer of the second adhesive between third and fourth panels effective to adhere the third panel to the fourth panel;

heating the second adhesive layer, the third panel, and the fourth panel to a predetermined temperature;

inserting the first wedge between the third and fourth panels to separate the third and fourth panels by the first predetermined distance;

inspecting the second adhesive layer for failure when the third and fourth panels are separated by the first predetermined distance;

inserting the second wedge between the third and fourth panels to separate the third and fourth panels by the second predetermined distance;

inspecting the second adhesive layer for failure when the third and fourth panels are separated by the second predetermined distance.

16. The method of claim 15, wherein when failure is detected during inspection of the second adhesive layer and not the first adhesive layer, selecting the adhesive comprises selecting the first adhesive.

17. The method of claim 15, wherein the first predetermined distance is less than the second predetermined distance.

18. The method of claim 15, wherein the inspecting is performed less than about 30 seconds after the heating.

* * * * *